(12) United States Patent
Yamada et al.

(10) Patent No.: US 6,566,015 B1
(45) Date of Patent: May 20, 2003

(54) NON-AQUEOUS ELECTROLYTIC SALT AND NON-AQUEOUS ELECTROLYTIC SECONDARY BATTERY IN WHICH IT IS USED

(75) Inventors: Manabu Yamada, Okazaki (JP); Naohiro Kubota, Tokyo (JP); Tomoyuki Oikawa, Tokyo (JP); Yasunori Takeuchi, Tokyo (JP)

(73) Assignees: Denso Corporation, Kariya (JP); Asahi Denka Kogyo K.K., Tokyo (JP)

( * ) Notice: Subject to any disclaimer, the term of this patent is extended or adjusted under 35 U.S.C. 154(b) by 0 days.

(21) Appl. No.: 09/414,864

(22) Filed: Oct. 8, 1999

(30) Foreign Application Priority Data

| Oct. 9, 1998 | (JP) | 10-288065 |
| Jul. 13, 1999 | (JP) | 11-198680 |
| Sep. 10, 1999 | (JP) | 11-256672 |
| Sep. 10, 1999 | (JP) | 11-257574 |

(51) Int. Cl.$^7$ ............... H01M 6/16; H01M 6/04
(52) U.S. Cl. ............ 429/326; 429/199; 429/324; 429/330; 429/332; 429/333; 429/338
(58) Field of Search ............... 429/324, 325, 429/326, 330, 345, 332, 333, 199

(56) References Cited

U.S. PATENT DOCUMENTS

| 5,340,672 A | * | 8/1994 | Kubota et al. ............... 429/249 |
| 5,580,684 A | | 12/1996 | Yokoyama et al. |
| 5,691,084 A | | 11/1997 | Kita et al. |
| 5,916,708 A | * | 6/1999 | Besenhard et al. ......... 429/199 |
| 6,103,420 A | * | 8/2000 | Nakane et al. ............. 429/223 |

FOREIGN PATENT DOCUMENTS

| JP | 4-184870 | 7/1992 |
| JP | 7-282849 | 10/1995 |
| JP | 8-111238 | 4/1996 |

* cited by examiner

*Primary Examiner*—Patrick Ryan
*Assistant Examiner*—Julian Mercado
(74) *Attorney, Agent, or Firm*—Harness, Dickey & Pierce, PLC

(57) ABSTRACT

The prevent invention provides a non-aqueous electrolyte for batteries comprising the dissolving of an electrolytic salt in an organic solvent, wherein said organic solvent contains at least one type each of cyclic carbonate compound, alkyl mono-carbonate compound represented by chemical formula (1), alkylene bis-carbonate compound represented by chemical formula (2), glycol diether compound represented by chemical formula (3) ($R^6O$—$(R^7O)_n$—$R^8$) and phosphorous-containing organic compound.

The use of at least one type of glycol diether represented with this general formula is able to yield satisfactory output characteristics by lowering the internal resistance of the battery as a result of increasing the mobility of lithium ions at the solid-liquid interface.

7 Claims, 2 Drawing Sheets

NON-AQUEOUS ELECTROLYTIC SALT AND NON-AQUEOUS ELECTROLYTIC SECONDARY BATTERY IN WHICH IT IS USED

BACKGROUND OF THE INVENTION

1. Field of the Invention

The present invention relates to a battery electrolyte that can be used for the electrolyte of a battery, and a non-aqueous electrolytic secondary battery that can be used as a battery for electric cars and portable electronic devices.

2. Description of the Related Art

There is a need for technology that uses electrical power more effectively in consideration of energy conservation and environmental issues. In order to respond to this need, a means of storing electricity is required that is able to store large amounts of electricity and provide that stored electricity efficiently. Secondary batteries having a large discharge capacity and high discharge voltage while also being able to be repeatedly charged and discharged are optimum for use as such a means of storing electricity.

Lithium secondary batteries are one example of this type of secondary battery. In a lithium secondary battery, a charging reaction occurs during charging in which lithium ions are released from the positive electrode and occluded at the negative electrode during charging, while during discharging, a discharging reaction occurs in which lithium ions are released from the negative electrode and occluded at the positive electrode. In lithium secondary batteries, since both energy density and output density are high, a large discharge capacity and discharge voltage are obtained. In addition, lithium ion secondary batteries, in which a negative electrode active material composed of a carbon material is used for the negative electrode, are expected to be used for portable electronic devices, electric cars and other applications due to their long service life and excellent practicality.

In lithium secondary batteries, an electrolyte made by dissolving a supporting electrolytic (electrolytes salts) salt in an organic solvent is used as the electrolyte. The electrolyte of this type of non-aqueous electrolytic secondary battery may be made by dissolving a supporting electrolyte such as lithium hexafluorophosphate (LiPF$_6$) in an organic solvent of a cyclic carbonate compound such as ethylene carbonate or propylene carbonate. Since cyclic carbonate compounds have a high dielectric constant, the energy density and output density of the battery can be made to be extremely high.

However, due to the high viscosity of cyclic carbonate compounds, the mobility of the lithium ions is low. Consequently, organic solvent in which low-viscosity linear-carbonate compounds such as dimethylcarbonate and diethylcarbonate are mixed into these cyclic carbonate compounds are widely used. However, these linear-carbonate compounds have the shortcomings of being low molecular weight compounds which makes them susceptible to volatilization.

In addition, although attempts have been made to add low molecular weight ether compounds to electrolyte for the purpose of lowering the viscosity of the electrolyte, not only do they have the disadvantage of lowering cycle characteristics, but also end up lowering incombustibility, thereby causing problems in terms of safety.

Therefore, Japanese Unexamined Patent Publication (Kokai) No. 7-282849 discloses the improvement of shelf life and cycle characteristics while also reducing volatility by containing an alkylene bis-carbonate compound in an electrolyte. However, simply containing an alkylene bis-carbonate compound alone makes it difficult to sufficiently increase the incombustibility of the electrolyte. Thus, although this electrolyte has the required safety, that safety is not adequate.

On the other hand, Japanese Unexamined Patent Publication (Kokai) No. 4-184870 and Japanese Unexamined Patent Publication (Kokai) No. 8-111238 disclose the improvement of safety by using an ester phosphate like a linear alkyl phosphate or cyclic phosphate, and an organic solvent such as a halogen compound.

However, when phosphate ester is used for the primary solvent, a side reaction occurs at the negative electrode interface during charging causing the occlusion of lithium ions to not proceed efficiently. As the result, the battery performance, such as the energy density and the charging and discharging efficiency often decrease significantly.

On the other hand, when ethylene carbonate is used for the primary solvent and a small amount of phosphate ester is added, although the battery performance is not affected and has the required safety, the battery has the problem that the safety decreases. Thus, it was very difficult to reconcile the performance and the safety of the lithium secondary battery.

In addition, there have been no secondary battery that include phosphate esters or halogen compounds and that exhibit an excellent battery performance at temperatures outside the room temperature.

The present invention has been attained in view of the above circumstances. An object of the present invention is to provide an electrolyte that can make the battery performance such as the energy density and output density excellent, can highly maintain the performance at temperatures outside room temperature, and is excellent in incombustibility.

Another object of the present invention is to provide a non-aqueous electrolyte, and a non-aqueous electrolytic secondary battery that has an excellent battery performance such as energy density and the charging and discharging efficiency, cycle characteristic, etc., can maintain the battery performance at temperatures outside room temperature, and also is excellent in safety.

Another object of the present is to provide a non-aqueous electrolyte, and a non-aqueous electrolytic secondary battery in which it is used, that satisfies both high battery performance and safety in good balance as a result of examining the composition, mixing ratio and so forth of a non-aqueous electrolyte solvent that retains the battery characteristics of secondary batteries and has a high level of safety.

SUMMARY OF THE INVENTION

A first aspect of the present invention is a battery electrolyte wherein a supporting electrolyte is dissolved in an organic solvent, characterized in that said organic solvent contains (a) a cyclic carbonate compound (b) at least one type of alkyl mono-carbonate compounds represented by chemical formula (1) and alkylene bis-carbonate compounds represented by chemical formula (2), and (c) a phosphorous-containing organic compound:

$$R^1OC(=O)OR^2 \quad (1)$$

wherein, substitution groups $R^1$ and $R^2$ represent identical or different alkyl groups, and at least one of these has at least three carbon atoms; and:

$$R^3OC(=O)OR^4OC(=O)OR^5$$

wherein, substitution groups $R^3$ and $R^5$ represent identical or different alkyl groups and have 1 to 4 carbon atoms, and $R^4$ represents a straight chain or branched alkylene group having 1 to 3 carbon atoms.

Cyclic carbonate compounds are able to increase the dielectric constant and so forth of electrolytes. Consequently, they can be made to provide excellent battery characteristics such as being able to increase the energy density of the battery.

The alkyl mono-carbonate compound represented by chemical formula (1) is able to lower the viscosity of an electrolyte. Consequently, since this compound is able to increase the mobility of electrolyte ions and so forth, they can be made to provide excellent battery characteristics such as energy density and output density. In particular, this compound is able to enhance electrolyte performance at low temperatures since it is able to maintain the energy density of batteries at high levels even at low temperatures.

The alkylene bis-carbonate compound represented by chemical formula (2) is able to give the electrolyte excellent storage properties. This alkylene bis-carbonate compound is able to enhance electrolyte performance at high temperatures since it is able to give the electrolyte excellent storage properties at high temperatures, in particular.

The phosphorous-containing organic compound is able to increase the incombustibility of the electrolyte. Consequently, it is able to enhance the safety of the electrolytic salt.

Each of the above compounds are able to effectively demonstrate their functions without impairing the functions of the other compounds. Consequently, the battery electrolyte of the present aspect is able to demonstrate excellent battery performance with respect to energy density, output density and so forth, and, in addition to the battery performance being able to be maintained at a high level even at temperatures other than room temperature, has excellent incombustibility. A battery electrolyte containing the alkylene bis-carbonate compound represented by chemical formula (2) in particular has excellent volatility and storage properties.

Thus, according to the battery electrolyte of the present invention, a battery can be obtained having excellent battery performance, the battery performance is maintained at a high level even at temperatures other than room temperature, and it is extremely safe.

A second aspect of the present invention is a non-aqueous electrolytic secondary battery equipped with a positive electrode and negative electrode that allows release and occlusion of lithium ions, and an electrolyte juxtapositioned between said positive and negative electrodes that is made by dissolving a supporting electrolyte in an organic solvent, characterized in that said organic solvent contains (a) a cyclic carbonate compound, (b) at least one type of alkyl mono-carbonate compounds represented by the above-mentioned chemical formula (1) and alkylene bis-carbonate compounds represented by the above-mentioned chemical formula (2), and (c) a phosphorous-containing organic compound. It is preferable that said organic solvent contains both compounds represented by chemical formulas (1) and (2) as component (b).

In the non-aqueous electrolytic secondary battery of the present aspect, since the electrolyte used has a high dielectric constant, it has extremely good battery performance such as energy density, output density, charging and discharging efficiency and cycle characteristics. In addition, since that electrolyte performance is maintained at a high level at temperatures other than room temperature, battery performance is maintained at a high level even if used in a temperature environment other than room temperature. Since it has excellent incombustibility, the battery is also extremely safe.

Consequently, the non-aqueous electrolytic secondary battery of the present aspect has excellent battery performance such as energy density, output density, charging and discharging efficiency and cycle characteristics, and, in addition to that, the battery performance is able to be maintained not only at room temperature, but also, either in low temperature or high temperature environments, it is extremely safe. Since a non-aqueous electrolytic secondary battery, in which an electrolyte containing the alkylene bis-carbonate compound represented by chemical formula (2) in particular is used, is able to maintain a high level of battery performance even after long-term use since the electrolyte has very low volatility and good storage properties.

Thus, according to the non-aqueous electrolytic secondary battery of the present invention, battery reliability is extremely high since, in addition to being able to power portable electronic devices, electric cars and so forth with advanced functions, it can also be used with peace of mind regardless of the temperature of the environment.

As a result of additional studies to further improve the balance between battery performance and safety after inventing the above-mentioned first and second aspects, when the inventors of the present invention examined a non-aqueous electrolyte in which a cyclic carbonate compound, an alkylene bis-carbonate compound, an alkylene mono-carbonate compound, a glycol diether compound and a phosphorous-containing organic compound were mixed for the above-mentioned organic solvent as a non-aqueous for batteries in which supporting electrolyte is dissolved in organic solvent, it was found that a secondary battery is obtained having even better battery performance such as output characteristics and cycle characteristics while still maintaining safety, thereby leading to completion of a third aspect of the present invention.

The non-aqueous electrolyte of this third aspect is a non-aqueous electrolyte for batteries in which an electrolyte salt is dissolved in an organic solvent characterized by the organic solvent containing at least one type each of a cyclic carbonate compound, an alkylene bis-carbonate compound represented by the above-mentioned chemical formula (2), an alkyl mono-carbonate compound represented by the above-mentioned chemical formula (1), a glycol diether compound represented by chemical formula (3) below and a phosphorous-containing organic compound:

$$R^6O-(R^7O)_n-R^8 \qquad (3)$$

wherein, substitution groups $R^6$ and $R^8$ are alkyl groups having 1 to 8 carbon atoms that may or may not be substituted with a halogen atom, substitution group $R^7$ is an alkylene group having 2 to 4 carbon atoms that may or may not be substituted with a halogen atom, and n is $1 \leq n \leq 4$, provided that at least one of the substitution groups $R^6$, $R^7$ and $R^8$ is substituted with a halogen atom.

It is preferable that 5 to 35 vol % of each of the alkylene bis-carbonate compound represented by the above-mentioned chemical formula (2), the glycol diether compound represented by chemical formula (3) and the phosphorous-containing organic compound be contained assuming the total amount of the above-mentioned organic solvent to be 100 vol %.

It is preferable that the above-mentioned cyclic carbonate compound be contained at 20 to 50 vol % assuming the total amount of the above-mentioned organic solvent to be 100 vol %.

It is preferable that the alkyl mono-carbonate compound represented by the above-mentioned chemical formula (1) be contained at 30 to 50 vol % assuming the total amount of the above-mentioned organic solvent to be 100 vol %.

It is preferable that the above-mentioned phosphorous-containing organic compound contain at least one type of organic compound selected from the group consisting of phosphate esters, phosphonate esters or phosphinate esters.

It is preferable that the above-mentioned electrolyte be composed of one type or a combination of at least two or more types of salts selected from the group consisting of inorganic salt composed of lithium ion and an anion selected from among $PF_6^-$, $BF_4^-$, $ClO_4^-$ and $AsF_6^-$, and an organic salt composed of a lithium ion and an anion selected from among $SO_3CF_3^-$, $N(CF_3SO_2)_2^-$, $C(CF_3SO_2)_3^-$ and their derivatives.

A fourth aspect of the present invention is a non-aqueous electrolytic secondary battery having a non-aqueous electrolyte, positive electrode and negative electrode, characterized by the use of the non-aqueous electrolyte of the above-mentioned third aspect containing at least one type each of a cyclic carbonate compound, an alkylene bis-carbonate compound represented by chemical formula (2), an alkyl mono-carbonate compound represented by chemical formula (1), a glycol diether compound represented by chemical formula (3) and a phosphorous-containing organic compound as an organic solvent of a non-aqueous electrolyte.

A fifth aspect of the present invention is a non-aqueous electrolyte in which an electrolytic salt salt is dissolved in said organic solvent characterized in that the organic solvent contains at least one type of glycol diether selected from the glycol diethers represented by chemical formula (4) below:

$$R^9O-(R^{10}O)_n-R^{11} \quad (4)$$

wherein, $R^9$ and $R^{11}$ are alkyl groups having 1 to 8 carbon atoms that may or may not be substituted with a halogen atom, $R^{10}$ is an alkylene group having 1 to 8 carbon atoms that may or may not be substituted with a halogen group provided that at least one of $R^9$, $R^{10}$ and $R^{11}$ is substituted with a halogen atom, and n is $1 \leq n \leq 4$.

The use of at least one type of glycol diether represented by chemical formula (4) is able to yield satisfactory output characteristics by lowering the internal resistance of the battery as a result of increasing the mobility of lithium ions at the solid-liquid interface. The mechanism by which the addition of glycol diether represented by chemical formula (4) to non-aqueous electrolyte increases the mobility of lithium ions at the solid-liquid interface is thought to be the result of hydrogen atoms of the glycol diether represented by chemical formula (4) demonstrating a surface activator-like effect particularly as a result of being substituted by fluorine atoms, thereby increasing the affinity for the electrode of the non-aqueous electrolyte.

In addition, those glycol diether compounds represented by chemical formula (4) in which $R^9$ and $R^{11}$ are alkyl groups having no more than 3 carbon atoms, $R^{10}$ is an alkylene group having no more than 2 carbon atoms, and n is 2 or less are particularly preferable due to the excellent solubility of the electrolyte. Compounds in which $R^{11}$ is an alkyl group substituted with a fluorine atom are preferable due the large effect of lowering internal resistance. Although the details of this reason are unknown, it is thought that the ion-delivery and acceptance barrier on the electrode surface is lowered due to improved wettability of the electrode-electrolyte interface resulting from enhancement of the surface activator-like effect mentioned above.

Thus, use of the non-aqueous electrolyte of the present invention in a non-aqueous electrolytic battery makes it possible to improve the output characteristics and so forth of the battery.

Moreover, it is preferable that the above-mentioned organic solvent contains at least one type of compound selected from among, for example, carbonates, lactones, ethers, sulfolanes and dioxolanes. The use of a non-aqueous electrolyte to which has been added a substance that is able to increase the solubility of an electrolyte salt and the dielectric constant and viscosity of the electrolyte, like a carbonate, lactone, ether, sulfolane and dioxolane makes it possible to further enhance the performance of the battery.

Moreover, it is also preferable that the above-mentioned organic solvent contain at least one type of compound selected from among, for example, phosphate ester, phosphonate ester and phosphinate ester. The use of a non-aqueous electrolyte to which has been added a substance like phosphate ester, phosphonate ester and phosphinate ester that is able to improve the incombustibility of the non-aqueous electrolyte makes it possible to improve the safety of a non-aqueous electrolytic battery.

In addition, it is preferable that the above-mentioned electrolyte salt be at least one type of inorganic salt selected from the group consisting of, for example, $LiPF_6$, $LiBF_4$, $LiClO_4$ and $LiAsF_6$, organic salt selected from the group consisting of, for example, $LiSO_3CF_3$, $LiN(CF_3SO_2)_2$ and $LiC(CF_3SO_2)_3$, and derivatives of said organic salts. These electrolyte salts are able to enhance the properties of the electrolyte. For this reason, the use of an incombustible electrolyte in which these electrolyte salts are dissolved is able to further improve the performance of the battery.

A sixth aspect of the present invention is characterized by being a non-aqueous electrolytic secondary battery provided with the non-aqueous electrolyte of the above-mentioned fifth aspect. The non-aqueous electrolytic secondary battery of the present aspect has excellent output characteristics for the reasons previously described as a result of having a non-aqueous electrolyte containing at least one type of glycol diether selected from among the glycol diethers represented by chemical formula (4).

Thus, the use of the non-aqueous electrolytic secondary battery of the present invention for the battery of a portable electronic device, automobile or other application is able to drive those applications with satisfactory performance and satisfactory reliability.

DESCRIPTION OF THE PREFERRED EMBODIMENTS

Figure 1:
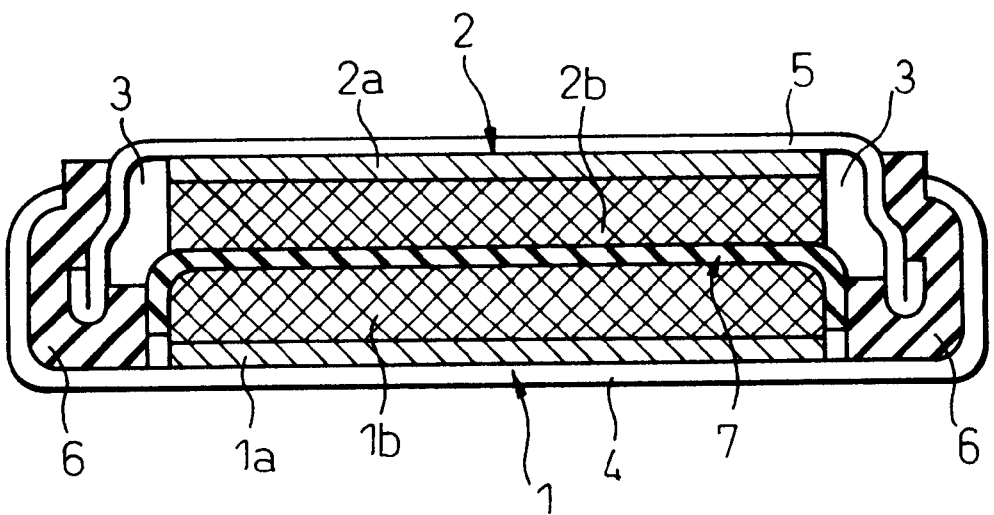
FIG. 1 is a schematic cross-sectional view of a coin-shaped battery demonstrating a non-aqueous electrolytic secondary battery of the present example.

The battery electrolyte of the first aspect of the present invention places no particular restrictions on the type of battery that is used, and can be used in known types of batteries. The battery may be a primary battery or secondary battery.

In the battery electrolyte of the present aspect, there are no particular restrictions on the type of cyclic carbonate compound, and compounds such as ethylene carbonate and propylene carbonate can be used.

There are also no particular restrictions on the type of the alkyl mono-carbonate compounds, and compounds such as ethyl-n-butylcarbonate, methyl-t-butylcarbonate, di-i-propylcarbonate and t-butyl-i-propylcarbonate can be used either alone or as a combination of two or more types.

There are no particular restrictions on the type of alkylene bis-carbonate compound, and compounds such as 1,2-bis(methoxycarbonyloxy)ethane, 1,2-bis(ethoxycarbonyloxy)ethane and 1,2-bis(ethoxycarbonyloxy)propane can be used either alone or as a combination of two or more types.

There are no particular restrictions on the type of the phosphorous-containing organic compound, and straight-chain or cyclic phosphate esters such as trimethylphosphate, triethylphosphate, tricresylphosphate, ethylenemethylphosphate and ethyleneethylphosphate can be used either alone or as a combination of two or more types.

It is preferable that both alkyl mono-carbonate compound and alkylene bis-carbonate compound be contained in the battery electrolyte of the present aspect. This battery electrolyte is able to maintain a high level of excellent battery performance not only at room temperature, but also in both low temperature and high temperature ranges. As a result, the temperature range over which excellent battery performance is obtained is expanded, enabling the battery to be more practical.

In addition, although there are no particular restrictions on the content of at least one type of alkyl mono-carbonate compounds represented by chemical formula (1) and alkylene bis-carbonate compounds represented by chemical formula (2) in the battery electrolyte of the present invention, assuming the total amount of organic solvent to be 100 vol %, it is preferable that the content be 5 to 50 vol %, and more preferably 30 to 50 vol %.

This battery electrolyte is able to yield battery performance that is better than that of the prior art, and in addition to being able to maintain that battery performance at a higher level than the prior art even at temperatures outside room temperature, it also yields extremely favorable incombustibility. The reason for this is believed to be that, due to the suitable balance between the content of at least one type of alkyl mono-carbonate compound represented by chemical formula (1) and alkylene bis-carbonate compound represented by chemical formula (2) and the content of cyclic carbonate compound and phosphorous-containing organic compound, its function can be demonstrated efficiently.

There are no particular restrictions on the type of the above-mentioned phosphorous-containing organic compound and its content, and said phosphorous-containing organic compound is at least one type of straight chain or cyclical phosphate ester compound, and its content is preferably 5 to 35 vol %, and more preferably 25 to 35 vol %, assuming the total amount of organic solvent to be 100 vol %.

This battery electrolyte can yield even better battery performance, and in addition to being able to maintain that battery performance at an even higher level at temperatures outside room temperature, it also has excellent incombustibility. The reason for this is believed to be that, due to the suitable balance between the content of that type of phosphorous-containing organic compound and the content of cyclical carbonate compound and at least one type of alkyl mono-carbonate compound represented by chemical formula (1) and alkylene bis-carbonate compound represented by chemical formula (2), its function can be demonstrated efficiently.

Moreover, there are no particular restrictions on the type of supporting electrolyte, and although its examples include $LiPF_6$, $LiBF_4$, $LiClO_4$, $LiAsF_6$, $LiI$, $LiAlCl_4$, $NaClO_4$, $NaBF_4$, $NaI$, $LiSO_3CF_3LiC(SO_2CF_3)_3$, $LiN(SO_2CF_3)_2$ and their derivatives, it is preferably at least one type of inorganic salt selected from the group consisting of $LiPF_6$, $LiBF_4$, $LiClO_4$ and $LiAsF_6$, derivatives of said inorganic salt, organic salt selected from the group consisting of $LiSO_3CF_3$, $LiC(SO_2CF_3)_3$, $LiN(SO_2CF_3)_2$ and derivatives of said organic salt.

This battery electrolyte is also able to yield excellent battery performance, and in addition to being able to maintain that battery performance at an even higher level even at temperatures outside room temperature, it also has excellent incombustibility.

There are no particular restrictions on the concentration of supporting electrolyte, and it is preferably suitably selected in consideration of the types of supporting electrolyte and organic solvent according to the particular application.

The non-aqueous electrolytic secondary battery of the second aspect of the present invention is composed of non-aqueous electrolyte, positive electrode, negative electrode and separator.

The electrolyte of the first aspect is used for the non-aqueous electrolyte. There are no particular restrictions on constituent features other than the non-aqueous electrolyte, namely the positive electrode, negative electrode and so forth, and materials can be used that are used in known non-aqueous electrolytic secondary batteries.

The following provides an explanation of the positive electrode and negative electrode of the non-aqueous electrolytic secondary battery of the present aspect using examples. There are no particular restrictions on the material and composition of the positive electrode provided it allows lithium ions to be released during charging and occluded during discharging, and those of known material and composition can be used. It is particularly preferable to use a positive electrode in which a mixture obtained by mixing positive electrode active material, conducting material and binding agent is coated onto a collector.

There are no particular restrictions on the type of positive electrode active material, and it can be formed from a known positive electrode active material. Examples of positive electrode active materials include $TiS_2$, $TiS_3$, $MoS_3$, $FeS_2$, $Li_{(1-x)}MnO_2$, $Li_{(1-x)}Mn_2O_4$, $Li_{(1-x)}CoO_2$, $Li_{(1-x)}NiO_2$ and $V_2O_5$.

In particular, compound oxides of lithium and transition metal such as $Li_{(1-x)}MnO_2$, $Li_{(1-x)}Mn_2O_4$, $Li_{(1-x)}CoO_2$ and $Li_{(1-x)}NiO_2$ have superior performance as positive electrode active materials due to the superior dispersion performance of electrons and lithium ions. Consequently, the use of this type of compound oxide of lithium and transition metal for the positive electrode active material allows the obtaining of high charging and discharging efficiency and satisfactory cycle characteristics. The use of $Li_{(1-x)}MnO_2$ and $Li_{(1-x)}Mn_2O_4$ in particular enable costs to be reduced due to the abundance of manganese resources.

In addition, there are no particular restrictions on the material and composition of the negative electrode provided that lithium ions are occluded during charging and released during discharging, and those having a known material composition can be used, examples of which include lithium, lithium alloy, tin compounds, carbonaceous materials and electrically conductive polymers. It is particularly preferable to use a negative electrode in which a mixture obtained by mixing negative electrode active material, conducting material and binding agent is coated onto a collector.

There are no particular restrictions on the type of negative electrode active material, and can be formed from a known negative electrode active material. Examples of negative electrode active materials include inorganic compounds such as lithium, lithium alloy and tin compounds, carbonaceous materials and electrically conducting polymers.

In particular, highly crystalline carbonaceous materials such as natural graphite and artificial graphite have excellent performance as negative electrode active materials due to their excellent lithium ion occlusion performance and dispersion performance. Consequently, the use of this type of carbonaceous material for the negative electrode active material allows the obtaining of high charging and discharging efficiency and satisfactory cycle characteristics.

There are no particular restrictions on the shape of the non-aqueous electrolytic secondary battery having the above-mentioned constitution, and it can be of various shapes, including coin-shaped, cylindrical or square.

A non-aqueous electrolytic salt of the third aspect of the present invention is a solution in which an electrolyte is dissolved in an organic solvent, which solvent is composed by at least one type each of a cyclic carbonate compound, an alkylene bis-carbonate compound represented by chemical formula (2), an alkyl mono-carbonate compound represented by chemical formula (1), a glycol diether compound represented by chemical formula (3) and a phosphorous-containing organic compound.

The cyclic carbonate in the above-mentioned organic solvent fulfills the role of increasing the conductance of the electrolyte due to its high specific dielectric constant. Cyclic carbonate compound can give the above-mentioned property to the electrolyte by being contained in the organic solvent at 20 to 50 vol %.

The alkylene bis-carbonate compound represented by chemical formula (2) is able to lower the volatility of the entire electrolyte by being mixed into the electrolyte since it has a relatively high molecular weight. In addition, since it is able to give high-temperature shelf life to the electrolyte, it is able to enhance battery characteristics at high temperatures. The alkylene bis-carbonate compound represented by chemical formula (2) is able to give the above-mentioned properties to the electrolyte by being contained in the organic solvent at 5 to 35 vol %.

The alkyl mono-carbonate compound represented by chemical formula (1) is able to lower the viscosity of the electrolyte by being mixed into the electrolyte due to its relatively low molecular weight. Consequently, it is able to improve the mobility of electrolytic ions in the electrolyte and give excellent output density and other battery characteristics. Since this alkyl mono-carbonate compound represented by chemical formula (1) has low viscosity, it can give the above-mentioned properties to the electrolyte by being contained in the organic solvent at 30 to 50 vol %. In particular, electrolyte mixed with this compound are able to retain a high degree of battery performance even at low temperatures.

The glycol diether compound represented by chemical formula (3) contains a halogen atom for at least one alkyl group, the terminal of which preferably being substituted with a fluorine atom. For example, in the case of using a compound having a trifluoroalkyl group (and preferably a trifluoromethyl group or trifluoroethyl group, etc.) for each of $R^6$ and $R^8$ in chemical formula (3), the glycol diether compound demonstrates an effect resembling a surface activator at the electrode interface, enabling it to enhance wettability of the contact surfaces between the electrolyte and electrodes. As a result, it is able to increase affinity of the non-aqueous electrolyte for the electrodes, reduce resistance inside the battery and increase the mobility of lithium ions, thereby improving battery performance. The glycol diether compound represented by chemical formula (3) is able to give the above-mentioned properties to the electrolyte by being contained in the organic solvent at 15 to 35 vol %.

The phosphorous-containing organic compound is a compound that is able to give incombustibility, and is able to enhance the incombustibility of the electrolyte by being one component of the electrolyte. Consequently, it is able to increase the safety performance of the non-aqueous electrolytic secondary battery to a high level. The phosphorous-containing organic compound is able to give the above-mentioned property to the electrolyte by being contained in the organic solvent at 20 to 30 vol %. Furthermore, the above-mentioned vol % is the amount represented as a percentage of volume assuming the total amount of organic solvent to be 100 vol %. Deviation from the above-mentioned mixing ratio is not preferable since it prevents the desired electrolyte properties from being demonstrated.

There are no particular restrictions on the above-mentioned cyclic carbonate compound, alkylene bis-carbonate represented by chemical formula (2) and alkyl mono-carbonate compound represented by chemical formula (1), and the each of the same compounds as used in the above-mentioned first aspect can be used.

There are no particular restrictions on the type of glycol diether compound represented by chemical formula (3), and compounds such as ethyleneglycol bis(trifluoroethyl)ether, i-propyleneglycol bis(trifluoroethyl)ether, ethyleneglycol bis(trifluoromethyl)ether, and diethyleneglycol bis(trifluoroethyl)ether.

In addition, it is preferable that at least one type of phosphorous-containing organic compound selected from the group consisting of phosphate ester, phosphonate ester or phosphinate ester is used for the phosphorous-containing organic compound. More specifically, phosphate esters such as trimethylphosphate and triethylphosphate, phosphonate esters such as diethylmethane phosphonate and di-(2,2,2-trifluoroethyl)methane phosphonate, and phosphinate esters can be used, or a mixture of a plurality of these compounds may be used.

There are no particular restrictions on the synthesis method of the above-mentioned organic compounds, and they may be synthesized using any routinely used synthesis method.

The example of the electrolytic salt used in the present aspect is the same as that indicated in the first aspect.

It is preferable that the above-mentioned electrolytic salt be dissolved in the above-mentioned organic solvent so that its concentration in the electrolyte is 0.1 to 3.0 moles/liter, and particularly 0.5 to 2.0 moles/liter. If the concentration in electrolyte is less than 0.1 moles/liter, sufficient current density is unable to be obtained, while if the concentration in electrolyte exceeds 3.0 moles/liter, the viscosity of the electrolyte increases thereby preventing its properties from being sufficiently obtained.

The non-aqueous electrolyte of the present aspect contains at least one type each of cyclic carbonate compounds, alkylene bis-carbonate compounds represented by chemical formula (2), alkyl mono-carbonate compounds represented by chemical formula (1), glycol diether compounds represented by chemical formula (3) and phosphorous-containing organic compounds in organic solvent. Consequently, the advantages of each mixed component can respectively be demonstrated. As a result, a secondary battery using this non-aqueous electrolyte is able to exhibit stable battery performance even at temperatures outside room temperature, while also being able to satisfy safety performance (since it has incombustibility). This electrolyte can be used in a first and a second battery.

The fourth aspect of the present invention is a non-aqueous electrolytic secondary battery that uses the non-aqueous electrolyte of the above-mentioned third aspect, and has the same constitution as the second aspect with respect to composite materials, positive electrode, negative electrode and separator, but not with respect to the electrolyte.

There are no particular restrictions on the shape of the non-aqueous electrolytic secondary battery of the present aspect having the above-mentioned constitution, and it can be of various shapes, including coin-shaped, cylindrical or square. FIG. 1 shows an example of a coin-shaped non-aqueous electrolytic secondary battery of the present invention, while FIG. 2 shows an example of a cylindrical non-aqueous electrolytic secondary battery of the present invention.

The organic solvent in the fifth aspect of the present invention contains at least one type of glycol diether represented by chemical formula (4). There are no particular restrictions on the alkyl groups represented with $R^9$ and $R^{11}$, having 1 to 8 carbon atoms and in which hydrogen atoms may or may not be substituted with halogen atoms, in the glycol diether represented by chemical formula (4). Examples of alkyl groups not having halogen atoms include straight chain or branched alkyl groups such as methyl, ethyl, propyl and butyl groups, while examples of alkyl groups in which hydrogen is substituted with halogen atoms include trifluoromethyl, 1,1,1-trifluoroethyl, 1,1,1,2,2-pentafluoroethyl and 1,1,1,3,3,3-hexafluoroisopropyl groups.

There are also no particular restrictions on the alkylene group represented with $R^{10}$, having 1 to 8 carbon atoms and in which hydrogen atoms may or may not be substituted with halogen atoms, in the glycol diether represented by chemical formula (4). Examples of alkylene groups not having halogen atoms include methylene, ethylene, propylene, trimethylene, tetramethylene and pentamethylene groups, while examples of alkylene groups in which hydrogen is substituted with halogen atoms include 2,2-bis(trifluoromethyl)propylene, 1,1,2,2,3,3-hexafluoropropylene, 1-fluoromethylethylene, 1-difluoromethylethylene and 2,2-difluoropropylene groups.

Specific preferable examples of these glycol diethers include the glycol diethers of No. 1 through No. 6 shown in Table 1.

TABLE 1

| No. 1 | $CF_3CH_2OCH_2CH_2OCH_2CF_3$ |
|---|---|
| No. 2 | $CF_3CH_2OCH_2CH(CH_3)OCH_2CF_3$ |
| No. 3 | $CH_3OCH_2CF_2CH_2OCH_3$ |
| No. 4 | $CF_3OCH_2CH_2OCF_3$ |
| No. 5 | $CF_3CH_2O(CH_2CH_2O)_2CH_2CF_3$ |
| No. 6 | $CF_3CH_2OCH_2CF_2CH_2OCH_2CF_3$ |

The non-aqueous electrolyte of the present aspect may use an organic solvent comprised only of the glycol diether represented by chemical formula (4), or may also be mixed with other organic solvent to increase the dielectric constant and electrical conductivity or to enhance safety. Since the above-mentioned glycol diether has excellent compatibility with other organic solvents, it can be easily mixed with other organic solvents.

Furthermore, there are no particular restrictions on the synthesis method of the above-mentioned glycol diether, and any known synthesis method can be used.

In the present invention, the organic solvent may contain carbonates, lactones, ethers, sulfolanes, dioxolanes, ketones, nitriles, halogenated hydrocarbons and so forth. It is preferable that the organic solvent contain at least one type of compound selected from the group consisting of carbonates, lactones, ethers, sulfolanes and dioxolanes. These compounds offer the advantage of improving the solubility of the electrolytic salt, improving the dielectric constant of the non-aqueous electrolyte or lowering the viscosity of the non-aqueous electrolyte.

There are no restrictions on any of the carbonates, lactones, ethers, sulfolanes and dioxolanes, and known compounds can be used, examples of which are listed below.

Examples of carbonates include dimethyl carbonate, methylethyl carbonate, diethyl carbonate, ethylene carbonate, propylene carbonate, ethyleneglycol dimethylcarbonate, propyleneglycol dimethylcarbonate, ethyleneglycol diethylcarbonate and vinylene carbonate.

Examples of lactones include γ-butyllactone. Examples of ethers include tetrahydrofuran, 2-methyltetrahydrofuran and 1,4-dioxane. Examples of sulfolanes include sulfolane and 3-methylsulfolane. Examples of dioxolanes include 1,3-dioxolane.

There are no restrictions on the ketones, nitriles or halogenated hydrocarbons, and known compounds can be used, examples of which include the compounds indicated below.

Examples of ketones include 4-methyl-2-pentanone. Examples of nitriles include acetonitrile, propionitrile, valeronitrile and benzoitrile. Examples of halogenated hydrocarbons include 1,2-dichloroethane.

Moreover, other compounds they may be contained in the organic solvent include methylformate, dimethylformamide and dimethylsulfoxide.

As has been described above, the non-aqueous electrolyte of the present invention may be mixed with other compounds in addition to the glycol diether represented with the above-mentioned chemical formula (4). At this time, although there are no particular restrictions on the content of this glycol diether, the glycol diether is preferably contained at 1 to 80 vol %, and particularly preferably at 5 to 50 vol %, relative to the total amount of the above-mentioned organic solvent.

Moreover, it is preferable to mix at least one type of phosphorous-containing compound selected from the group consisting of substances that give incombustibility to the non-aqueous electrolyte such as phosphate ester, phosphonate ester or phosphinate ester to enhance safety. More specifically, this may be a phosphate ester such as trimethylphosphate or triethylphosphate, a phosphonate ester such as diethylmethanephosphonate or di-(2,2,2-trifluoroethyl)methanephosphonate, phosphinate ester or a mixture of a plurality of these compounds.

There are no particular restrictions on the type of electrolyte used in the non-aqueous electrolyte of the present aspect, and known electrolytic salts can be used. Examples of electrolytic salts that can be used include inorganic salts such as $LiPF_6$, $LiBF_4$, $LiClO_4$, $LiAsF_6$, LiI, $LiAlCl_4$, $NaClO_4$, $NaBF_4$ and NaI, organic salts such as $LiSO_3CF_3$, $LiN(SO_2CF_3)_2$ and $LiC(SO_2CF_3)_3$ and derivatives of these organic salts.

Among these electrolytic salts, inorganic salts selected from the group consisting of $LiPF_6$, $LiBF_4$, $LiClO_4$ and $LiAsF_6$, organic salts selected from the group consisting of $LiSO_3CF_3$, $LiN(SO_2CF_3)_2$ and $LiC(SO_2CF_3)_3$, and derivatives of these organic salts are particularly preferable. This is because a non-aqueous electrolytic secondary battery that uses at least one type of these electrolytic salts in the non-aqueous electrolyte has excellent electrical characteristics.

There are no particular restrictions on the concentration of electrolytic salt dissolved in the electrolyte. Although the concentration can be suitably selected according to the particular application, it is preferably 0.1 to 3.0 moles/liter. If the concentration of electrolytic salt is lower than 0.1 moles/liter, sufficient current density may not be obtained. If the concentration of electrolytic salt is greater than 3.0 moles/liter, there may be a risk of hindering the stability of the electrolyte. If the concentration of the electrolytic salt is 0.5 to 2.0 moles/liter in particular, it is possible to obtain sufficient current density and reliable stability of the electrolyte.

The non-aqueous electrolyte of the present aspect can be prepared by dissolving an electrolytic salt such as the above-mentioned electrolytic salt in organic solvent in which the above-mentioned phosphorous-containing compound and the above-mentioned other organic solvents are mixed into the above-mentioned glycol diether as necessary according to a known method.

There are no particular restrictions on the type of non-aqueous electrolytic battery that can be used with the non-aqueous electrolyte of the present aspect, and although any known non-aqueous electrolytic battery can be used, the use of a lithium battery is particularly preferable. In addition, the non-aqueous electrolyte of the present aspect may be used in a primary battery or in a secondary batter. Its use in a non-aqueous electrolytic secondary battery to be described later is particularly preferable.

A sixth aspect of the present invention is a non-aqueous electrolytic secondary battery that uses the non-aqueous electrolyte of the above-mentioned fifth aspect, and has the same constitution as the second aspect with respect to composite materials, positive electrode, negative electrode and separator, but not with respect to the electrolyte.

Although the following provides a detailed explanation of the present invention through its examples, the present invention is not restricted by these examples.

EXAMPLE 1

Ethylene carbonate (EC), diisopropylene carbonate (DIPC) and triethylphosphate (TEP) were respectively mixed at equal volume ratios to first prepare the organic solvent. $LiPF_6$ was dissolved in this organic solvent at a concentration of 1 mole/liter to obtain a battery electrolyte.

EXAMPLE 2

EC, ethyl-n-butylcarbonate (E—n—BC) and TEP were respectively mixed at equal volume ratios to first prepare the organic solvent. $LiPF_6$ was dissolved in this organic solvent at a concentration of 1 mole/liter to obtain a battery electrolyte.

EXAMPLE 3

EC, 1,2-bis(ethoxycarbonyloxy)ethane (1,2-B(ECO)E) and TEP were respectively mixed at equal volume ratios to first prepare the organic solvent. $LiPF_6$ was dissolved in this organic solvent at a concentration of 1 mole/liter to obtain a battery electrolyte.

EXAMPLE 4

EC, 1,2-bis(methoxycarbonyloxy)propane (1,2-B(MCO)P) and TEP were respectively mixed at equal volume ratios to first prepare the organic solvent. $LiPF_6$ was dissolved in this organic solvent at a concentration of 1 mole/liter to obtain a battery electrolyte.

EXAMPLE 5

EC and diethylcarbonate (DEC) were respectively mixed at equal volume ratios to first prepare the organic solvent. $LiPF_6$ was dissolved in this organic solvent at a concentration of 1 mole/liter to obtain a battery electrolyte.

EXAMPLE 6

EC and DIPC were respectively mixed at equal volume ratios to first prepare the organic solvent. $LiPF_6$ was dissolved in this organic solvent at a concentration of 1 mole/liter to obtain a battery electrolyte.

EXAMPLE 7

EC and 1,2-B(ECO)E were respectively mixed at equal volume ratios to first prepare the organic solvent. $LiPF_6$ was dissolved in this organic solvent at a concentration of 1 mole/liter to obtain a battery electrolyte.

EXAMPLE 8

EC and TEP were respectively mixed at equal volume ratios to first prepare the organic solvent. $LiPF_6$ was dissolved in this organic solvent at a concentration of 1 mole/liter to obtain a battery electrolyte.

EXAMPLE 9

EC, DIPC and 1,2-B(ECO)E were respectively mixed at equal volume ratios to first prepare the organic solvent. $LiPF_6$ was dissolved in this organic solvent at a concentration of 1 mole/liter to obtain a battery electrolyte.

EXAMPLE 10

DIPC, 1,2-B(ECO)E and TEP were respectively mixed at equal volume ratios to first prepare the organic solvent. $LiPF_6$ was dissolved in this organic solvent at a concentration of 1 mole/liter to obtain a battery electrolyte.

EXAMPLE 11

EC at 33 vol %, DIPC at 17 vol %, 1,2-B(ECO)E at 17 vol % and TEP at 33 vol % were respectively mixed to first prepare the organic solvent. $LiPF_6$ was dissolved in this organic solvent at a concentration of 1 mole/liter to obtain a battery electrolyte.

EXAMPLE 12

EC at 30 vol %, DIPC at 20 vol %, 1,2-B(ECO)E at 20 vol % and TEP at 30 vol % were respectively mixed to first prepare the organic solvent. LiPF$_6$ was dissolved in this organic solvent at a concentration of 1 mole/liter to obtain a battery electrolyte.

EXAMPLE 13

EC, DIPC, 1,2-B(ECO)E and TEP were respectively mixed at equal volume ratios to first prepare the organic solvent. LiPF$_6$ was dissolved in this organic solvent at a concentration of 1 mole/liter to obtain a battery electrolyte.

EXAMPLE 14

EC at 33 vol %, E—n—BC at 17 vol %, 1,2-B(MCO)P at 20 vol % and TEP at 33 vol % were respectively mixed to first prepare the organic solvent. LiPF$_6$ was dissolved in this organic solvent at a concentration of 1 mole/liter to obtain a battery electrolyte.

EXAMPLE 15

EC at 33 vol %, E—n—BC at 17 vol %, 1,2-B(MCO)P at 17 vol % and ethyleneethyl phosphate (EEP) at 33 vol % were respectively mixed to first prepare the organic solvent. LiPF$_6$ was dissolved in this organic solvent at a concentration of 1 mole/liter to obtain a battery electrolyte.

The compositions of the organic solvents of each of the battery electrolyte obtained above are summarized in Table 2.

electrolyte, hung for 3 minutes in air to remove any excess battery electrolyte remaining on the manila paper by allowing it to drip off.

Next, a sample board was prepared having a support needle that can be poked through the pieces of manila paper so that they are arranged in a row. Each of the pieces of manila paper impregnated with electrolyte were then poked onto the support needle of the sample board at 25 mm intervals and placed horizontally. This sample board was then placed in a metal box measuring 250×250×500 mm, and one end was ignited with a lighter.

The rate at which combustion moved in the lengthwise direction of the manila paper at that time (to simply be referred to as the combustion rate) was then measured to evaluate the incombustibility of each battery electrolyte.

Viscosity Evaluation Method

The viscosity of each battery electrolyte was measured with a capillary viscosimeter at 20° C.

High-Temperature Storage Properties Evaluation Method

A piece of lithium metal was immersed in each battery electrolyte and held in the battery electrolyte for 50 hours at 60° C. Changes in the color of the electrolyte were observed before and after this high-temperature shelf test.

TABLE 2

| Example No. | Solvent Composite Ratio 0% — 50% — 100% | | |
|---|---|---|---|
| 1 | EC | DIPC | TEP |
| 2 | EC | E-n-BC | TEP |
| 3 | EC | 1,2-B(ECO)E | TEP |
| 4 | EC | 1,2-B(MCO)P | TEP |
| 11 | EC | DIPC / 1,2-B(ECO)E | TEP |
| 12 | EC | DIPC / 1,2-B(ECO)E | TEP |
| 13 | EC | DIPC / 1,2-B(ECO)E | TEP |
| 14 | EC | E-n-BC / 1,2-B(MCO)P | TEP |
| 15 | EC | E-n-BC / 1,2-B(MCO)P | EEP |
| 5 | EC | | DEC |
| 6 | EC | | DIPC |
| 7 | EC | | 1,2-B(ECO)E |
| 8 | EC | | TEP |
| 9 | EC | DIPC | 1,2-B(ECO)E |
| 10 | DIPC | 1,2-B(ECO)E | TEP |

Electrolytic Salt Flame Retardancy Evaluation Method

The combustion rate test described below was performed to investigate the incombustibility of each of the battery electrolyte obtained in the above example.

To begin with, pieces of manila paper for use as separators cut to a width of 15 mm and length of 320 mm and having a thickness of 0.04 mm were immersed in each battery electrolyte to impregnate the manila paper with electrolyte. Next, the pieces of manila paper were pulled out of each Production of Non-Aqueous Electrolytic Secondary Battery Next, a coin-shaped non-aqueous electrolytic secondary battery as schematically shown in FIG. 1 was produced using each of the battery electrolytes obtained in the manner described above. Each said non-aqueous electrolytic secondary battery was equipped with positive electrode 1 and negative electrode 2 allowing release and occlusion of lithium ions, and electrolyte 3 juxtapositioned between positive electrode 1 and negative electrode 2.

In this battery, positive electrode 1, negative electrode 2 and electrolyte 3 were sealed by means of gaskets 6 made of polypropylene within electrode case 4 and negative electrode case 5, respectively, made of stainless steel. This battery was produced in the manner described below.

Positive electrode 1 was formed in the manner described below.

N-methyl-2-pyrrolidone (NMP) was added into a mixture of 90 parts by weight of $LiMnO_2$ and 10 parts by weight of polyvinylidene fluoride and kneaded to obtain a slurry. This slurry was coated onto positive electrode collector 1a made of aluminum and dried followed further by press forming to obtain positive electrode 1.

Negative electrode 2 was produced in the manner described below.

NMP was added into a mixture of 90 parts by weight of carbon powder and 10 parts by weight of polyvinylidene fluoride and kneaded to obtain a slurry. This slurry was coated onto negative electrode collector 2a made of copper and dried followed further by press forming to obtain negative electrode 2.

Positive electrode 1 and negative electrode 2 obtained in the manner described above were welded to positive electrode case 4 and negative electrode case 5, respectively, and these welded bodies were laminated with separator 7 in between. Thereafter, after charging electrolyte 3 into the prescribed location, the electrolyte was sealed with gaskets 6 to complete the non-aqueous electrolytic secondary battery shown in FIG. 1.

Furthermore, the battery of the present invention is not limited to only the coin-shaped battery used in the above-mentioned example, but the same results can be obtained even with, for example, the cylindrical battery shown in FIG. 2.

Figure 2A:
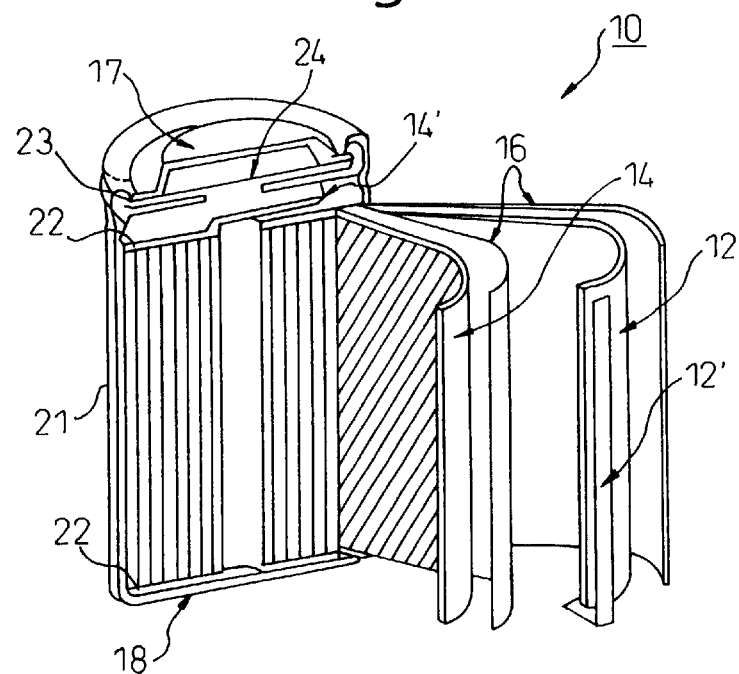
FIG. 2 is a schematic drawing of a cylindrical battery demonstrating a summary of a non-aqueous electrolytic secondary battery of the present example, with FIG. 2A being a cross-sectional perspective view of a tubular battery, and FIG. 2B being a schematic illustration providing an explanation of the electrode section.
Figure 2B:
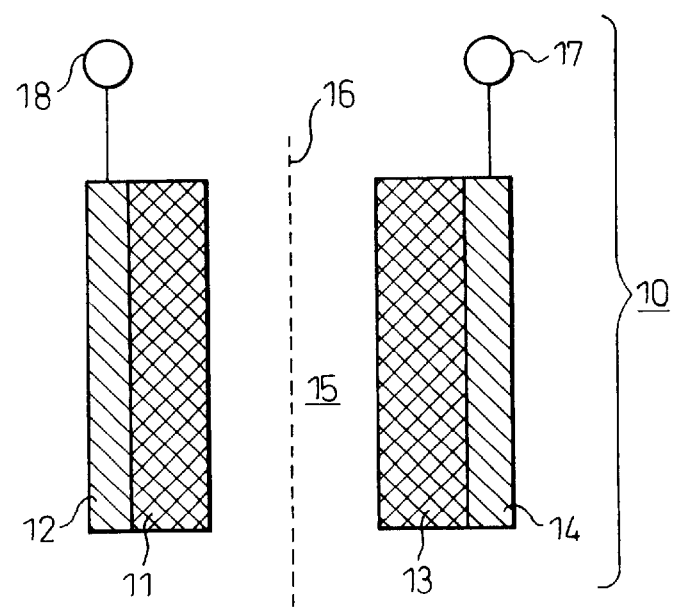

FIG. 2 is a conceptual drawing of the cylindrical shape of the non-aqueous electrolytic secondary battery of the present invention, while FIG. 2A is a cross-sectional, perspective schematic drawing of that battery, and FIG. 2B is an explanatory schematic drawing showing the electrode portion.

In cylindrical non-aqueous electrolytic secondary battery 10, the same positive and negative electrodes as those produced in the coin-shaped battery are used in the form of sheets, both are laminated with a separator in between, and a large number are wound in the form of a coil, and contained in a case having a prescribed cylindrical shape.

Namely, as shown in FIG. 2B, the electrode constitution consists of negative electrode mixture 11 formed on negative electrode collector 12 and positive electrode mixture 13 formed on positive electrode collector 14 arranged so that the surfaces of the mixtures are opposing each other, with separator 16 and electrolyte 15 placed between them, which are wound in the form of a coiled body, and contained in the battery case shown in FIG. 2A separated from said battery case by an insulating sheet.

Negative electrode lead 12' is welded to the end of negative electrode collector 12 of this coiled body, and nickel negative electrode terminal 18 is welded to the end of case 21 with current blocking thin plate 22 between said negative electrode terminal 18 and said case 21. On the other hand, an aluminum positive electrode terminal 17 is attached to the end of positive electrode lead 14' welded to positive electrode collector 14, and fixed on the end with current blocking thin plate 22 between said positive electrode terminal 17 and said case 21, in the form of a battery cover. As a result, the bottom of case 21 serves as negative electrode terminal 18, while the case cover serves as positive electrode terminal 17. The above-mentioned non-aqueous electrolyte 15 is filled into the coiled body contained in case 21, sealed with gasket 23 and provided with safety cover 24 to form a cylindrical non-aqueous electrolytic secondary battery having a diameter of 18 mm and height of 65 mm.

Furthermore, when preparing a cylindrical battery, the positive electrode, negative electrode and electrolyte are prepared in the same manner as described above, and after sequentially layering the above-mentioned positive and negative electrodes while using a microporous polyethylene film having a thickness of 25 $\mu$m as a separator, the electrodes are repeatedly wrapped numerous times into the form of a coil to form a coiled body. Next, an insulator is inserted into the bottom of the battery case after which the above-mentioned coiled body is housed in said battery case. The terminals of the negative and positive electrodes are connected to the bottom and cover of the battery case, and the above-mentioned non-aqueous electrolyte is filled into the battery case prepared in the above manner and sealed to produce a cylindrical non-aqueous electrolytic secondary battery.

In the above-mentioned example, evaluation was performed with a secondary battery produced in the shape of a coin.

Measurement of Discharge Capacity and Internal Resistance of Non-Aqueous Electrolytic Secondary Battery Each of the non-aqueous electrolytic secondary batteries using the battery electrolyte of Examples 1 through 15 were charged and discharged 50 times under the following charging and discharging conditions at temperatures of 20° C. and 60° C. each. The discharge capacity of each battery was measured at the initial stage (before the initial charging and discharging cycle) and after completion of 50 cycles of charging and discharging. The capacity maintenance rate after 50 cycles of charging and discharging with respect to the initial discharge capacity was calculated. In addition, the internal resistance of each battery was measured before and after 50 cycles of charging and discharging in an additional test conducted at 20° C.

In addition, a charging and discharging test was also conducted under the same charging and discharging conditions at 0° C. to measure the discharge capacity at the initial stage.

Charging and discharging conditions: After charging at a constant current of 1.1 $mA/cm^2$ as the current density per unit surface area of positive electrode 1 and final voltage of 4.2 V (CC), discharging was performed at a constant current of 1.1 $mA/cm^2$ and final voltage of 3.0 V (CC).

Results

The results of each of the above tests are shown in Table 3.

TABLE 3

| Ex. No. | Combustion rate (mm/s) | Viscosity (cP) 20° C. | Coloring in High-temp. Shelf test | Discharge Capacity (mAh) (Initial) | | | Internal Resistance (Ω) | | Capacity Maintenance Rate (%) | |
|---|---|---|---|---|---|---|---|---|---|---|
| | | | | 20° C. | 60° C. | 0° C. | Init. value | After 50 cycles | 20° C. | 60° C. |
| 1 | <0.1 | 8.9 | Yes | 1.65 | 1.69 | 1.60 | 8.6 | 11.8 | 92.8 | 64.3 |
| 2 | <0.1 | 9.2 | Yes | 1.59 | 1.63 | 1.56 | 8.9 | 12.3 | 92.3 | 83.8 |
| 3 | <0.1 | 12.8 | No | 1.60 | 1.65 | 0.98 | 12.4 | 15.2 | 93.1 | 72.4 |
| 4 | <0.1 | 13.6 | No | 1.56 | 1.62 | 0.87 | 12.7 | 15.5 | 93.0 | 73.1 |
| 11 | <0.1 | 10.7 | No | 1.64 | 1.68 | 1.52 | 10.6 | 12.9 | 93.9 | 74.3 |
| 12 | <0.1 | 10.1 | No | 1.70 | 1.71 | 1.49 | 10.5 | 13.1 | 93.2 | 74.8 |
| 13 | <0.1 | 11.2 | No | 1.68 | 1.70 | 1.44 | 10.9 | 13.5 | 93.1 | 74.5 |
| 14 | <0.1 | 10.9 | No | 1.62 | 1.72 | 1.57 | 11.3 | 13.8 | 93.4 | 73.6 |
| 15 | <0.1 | 11.1 | No | 1.58 | 1.69 | 1.56 | 11.8 | 13.9 | 93.7 | 74.1 |
| 5 | 6.9 | 7.8 | Yes | 1.57 | 1.70 | 1.52 | 6.8 | 7.5 | 96.4 | 79.1 |
| 6 | 4.9 | 8.1 | Yes | 1.61 | 1.70 | 1.41 | 7.9 | 8.8 | 95.9 | 78.6 |
| 7 | 2.0 | 15.4 | No | 1.68 | 1.73 | 1.23 | 14.9 | 16.1 | 95.1 | 77.9 |
| 8 | <0.1 | 10.2 | Yes | 1.06 | 1.23 | 0.81 | 10.6 | 20.9 | 68.7 | 45.9 |
| 9 | 4.3 | 12.1 | No | 1.59 | 1.67 | 1.32 | 12.0 | 14.2 | 94.8 | 76.8 |
| 10 | 0.3 | 8.3 | No | 0.94 | 1.29 | 0.89 | 10.7 | 12.6 | 61.3 | 40.7 |

In the battery electrolyte of Examples 1 to 4 and 11 to 15, the combustion rates are all less than 0.1 m/s, and flames did not spread at all over the manila paper. Thus, the electrolyte of these examples can be seen to have extremely good incombustibility and a high degree of safety.

In addition, the battery electrolyte of Examples 3, 4 and 11 to 15 did not demonstrate any change in color even after the high-temperature shelf test. In addition, they also demonstrated a low level of volatility. Thus, the electrolyte of these examples can be seen to have excellent volatility and storage properties at high temperatures.

On the other hand, each of non-aqueous electrolyte used for the battery electrolytes of Examples 1 to 4 and 11 to 15 were found to have a high discharge capacity at 20° C. In addition, the capacity maintenance rates after 50 cycles of charging and discharging were also high. Thus, batteries using the electrolyte of these examples can be seen to demonstrate a high degree of battery performance at room temperature.

Each of the non-aqueous electrolytic secondary batteries that used the battery electrolyte of Examples 3, 4 and 11 and 15 exhibited little decrease in capacity maintenance rate after 50 cycles of charging and discharging at high temperatures.

In addition, each of the non-aqueous electrolytic secondary batteries that used the battery electrolyte of Examples 1, 2 and 11 to 15 were found to maintain a high level of discharge capacity at 0° C. Thus, batteries using the electrolyte of these examples can be seen to be able to maintain a high degree of battery performance even at low temperatures.

On the other hand, in the electrolyte of Examples 5 to 7 and 9, the combustion rate can be seen to be 2.0 mm/s or more in all cases. Although this level of incombustibility is within the allowed safety range, it cannot not necessarily be said to be high. A possible reason for obtaining these results is that neither diethyl carbonate, diisopropyl carbonate or 1,2-bis(methoxycarbonyloxy) ethane have an effect that increases incombustibility.

In contrast to these electrolyte of Examples 5 to 7 and 9, the electrolyte of Examples 8 and 10 have combustion rates of 0 mm/s and 0.3 mm/s indicating excellent imcombustibility and can be seen to have a high degree of safety.

However, in the non-aqueous electrolytic secondary battery using the battery electrolyte of Example 8 (not containing either an alkyl mono-carbonate compound or alkylene bis-carbonate compound), it can be seen that not very high values are obtained for both the discharge capacity and the capacity maintenance rate. In addition, internal resistance after 50 cycles of charging and discharging increased considerably large as compared with the initial value. A possible reason for the obtaining of these results is that, since triethyl phosphate has a larger number of donors than ethylene carbonate, triethyl-phosphate is believed to have selectively solvated to lithium ion. Consequently, there is greater susceptibility to the occurrence of side reactions at the negative electrode interface, which is thought to have resulting in greater consumption of lithium ions.

In addition, in the case of the non-aqueous electrolytic secondary battery using the battery electrolyte of Example 10 as well (not containing a cyclic carbonate compound), the value obtained for discharge capacity can be seen not to be very high. One reason for obtaining this result is the low electrical conductivity of the electrolyte.

Moreover, since an alkylene bis-carbonate compound is not contained in Examples 5 and 6, the electrolyte becomes discolored in the high-temperature shelf test. Since an alkyl mono-carbonate compound is not contained in Example 7, viscosity increases and internal resistance is high.

Thus, the battery electrolyte of Examples 5 to 10 are unable to realize both excellent discharge capacity and extremely outstanding safety.

According to the above results, the battery electrolyte of Examples 1 to 4 and 11 to 15 all yield excellent battery performance, and in addition to being able to maintain that high level of performance at temperatures outside room temperature, they can also be seen to allow the obtaining of an extremely high level of safety.

In addition, in all of the battery electrolyte of Examples 1 to 4, any one of the alkyl mono-carbonate compound represented with chemical formula (1) and the alkylene bis-carbonate compound represented with chemical formula (2) is contained at 30 to 50 vol % assuming the total amount of organic solvent to be 100 vol %. In addition, in all of the battery electrolyte of Examples 11 to 15, the alkyl mono-carbonate compound represented with chemical formula (1) and the alkylene bis-carbonate compound represented with chemical formula (2) are contained in total at 30 to 50 vol %.

Moreover, in all of the battery electrolyte of Examples 1 to 4 and 11 to 15, the phosphorous-containing organic compound is at least one type of straight chain or cyclic phosphate ester compound, and is contained at 25 to 35 vol %. In addition, $LiPF_6$ is used for the supporting electrolyte in each of these electrolyte as well.

In the battery electrolyte of Examples 1 to 4 and 11 to 15, each of these allow the obtaining of extremely outstanding battery performance due to the additional factors described above, and in addition to that battery performance being able to be maintained at an extremely high level even at temperatures outside of room temperature, these battery electrolyte also allow the obtaining of an extremely high level of safety.

In particular, the battery electrolyte of Examples 11 to 15 are able to maintain a high level of outstanding battery performance at both high and low temperatures. One reason for obtaining these results is that all of these electrolyte contain both the alkyl mono-carbonate compound represented with chemical formula (1) and the alkylene bis-carbonate compound represented with chemical formula (2)

EXAMPLE 16

Lithium hexafluorophosphate ($LiPF_6$) was dissolved in a mixed solvent of ethylene carbonate (EC) at 30 vol %, 1,2-bis(ethoxycarbonyloxy)ethane (1,2-B(ECO)E) at 10 vol %, ethyl-n-butylcarbonate (E—n—BC) at 40 vol %, ethyleneglycol bis(trifluoroethyl)ether (EGB(TFE)E) at 10 vol % and triethyl phosphate (TEP) at 10 vol % to a concentration of 1 mole/liter to prepare an electrolyte.

EXAMPLE 17

Lithium hexafluorophosphate ($LiPF_6$) was dissolved in a mixed solvent of EC at 30 vol %, 1,2-B(ECO)E at 10 vol %, E—n—BC at 40 vol %, EGB(TFE)E at 10 vol %, and DFEMP at 10 vol % to a concentration of 1 mole/liter to prepare an electrolyte.

EXAMPLE 18

Lithium hexafluorophosphate ($LiPF_6$) was dissolved in a mixed solvent of EC at 30 vol %, 1,2-bis(methoxycarbonyloxy) propane (1,2-B(MCO)P) at 10 vol %, E—n—BC at 40 vol %, EGB(TFE)E at 10 vol %, and TEP at 10 vol % to a concentration of 1 mole/liter to prepare an electrolyte.

EXAMPLE 19

Lithium hexafluorophosphate ($LiPF_6$) was dissolved in a mixed solvent of EC at 30 vol %, 1,2-B(ECO)E at 10 vol %, diisopropyl carbonate (DIPC) at 40 vol %, EGB(TFE)E at 10 vol %, and TEP at 10 vol % to a concentration of 1 mole/liter to prepare an electrolyte.

EXAMPLE 20

Lithium hexafluorophosphate ($LiPF_6$) was dissolved in a mixed solvent of EC at 30 vol %, 1,2-B(ECO)E at 10 vol %, E—n—BC at 30 vol %, EGB(TFE)E at 20 vol %, and TEP at 10 vol % to a concentration of 1 mole/liter to prepare an electrolyte.

EXAMPLE 21

Lithium hexafluorophosphate ($LiPF_6$) was dissolved in a mixed solvent of EC at 30 vol %, 1,2-B(ECO)E at 10 vol %, E—n—BC at 30 vol %, EGB(TFE)E at 10 vol %, and TEP at 20 vol % to a concentration of 1 mole/liter to prepare an electrolyte.

EXAMPLE 22

Lithium hexafluorophosphate ($LiPF_6$) was dissolved in a mixed solvent of equal volumes of EC and diethyl carbonate (DEC) to a concentration of 1 mole/liter to prepare an electrolyte.

EXAMPLE 23

Lithium hexafluorophosphate ($LiPF_6$) was dissolved in a mixed solvent of equal volumes of EC and TEP to a concentration of 1 mole/liter to prepare an electrolyte.

EXAMPLE 24

Lithium hexafluorophosphate ($LiPF_6$) was dissolved in a mixed solvent of 1,2-B(ECO)E at 20 vol %, E—n—BC at 40 vol %, EGB(TFE)E at 20 vol %, and TEP at 20 vol % to a concentration of 1 mole/liter to prepare an electrolyte.

EXAMPLE 25

Lithium hexafluorophosphate ($LiPF_6$) was dissolved in a mixed solvent of EC at 30vol %, E—n—BC at 50 vol %, EGB(TFE)E at 10 vol %, and TEP at 10 vol % to a concentration of 1 mole/liter to prepare an electrolyte.

EXAMPLE 26

Lithium hexafluorophosphate ($LiPF_6$) was dissolved in a mixed solvent of EC at 30 vol %, 1,2-B(ECO)E at 20 vol %, E—n—BC at 10 vol %, EGB(TFE)E at 20 vol %, and TEP at 20 vol % to a concentration of 1 mole/liter to prepare an electrolyte.

EXAMPLE 27

Lithium hexafluorophosphate ($LiPF_6$) was dissolved in a mixed solvent of EC at 30 vol %, 1,2-B(ECO)E at 10 vol %, E—n—BC at 50 vol % and TEP at 10 vol % to a concentration of 1 mole/liter to prepare an electrolyte.

EXAMPLE 28

Lithium hexafluorophosphate ($LiPF_6$) was dissolved in a mixed solvent of EC at 30 vol %, 1,2-B(ECO)E at 10 vol %, E—n—BC at 50 vol % and EGB(TFE)E at 10 vol % to a concentration of 1 mole/liter to prepare an electrolyte.

The composite ratios of each of the non-aqueous electrolyte prepared in the above-mentioned examples are shown in Table 4.

TABLE 4

| Example No. | 0% | | | 50% | | | | 100% |
|---|---|---|---|---|---|---|---|---|
| 16 | EC | 1,2-B(ECO)E | | E-n-BC | | | EGB(TFE)E | TEP |
| 17 | EC | 1,2-B(ECO)E | | E-n-BC | | | EGB(TFE)E | TEP |
| 18 | EC | 1,2-B(ECO)E | | E-n-BC | | | EGB(TFE)E | TEP |
| 19 | EC | 1,2-B(ECO)E | | DIPC | | | EGB(TFE)E | TEP |
| 20 | EC | 1,2-B(ECO)E | | E-n-BC | | EGB(TFE)E | | TEP |
| 21 | EC | 1,2-B(ECO)E | | E-n-BC | | EGB(TFE)E | TEP | |
| 22 | EC | | | | DEC | | | |
| 23 | EC | | | | TEP | | | |
| 24 | 1,2-B(ECO)E | | E-n-BC | | | EGB(TFE)E | | TEP |
| 25 | EC | | | E-n-BC | | | EGB(TFE)E | TEP |
| 26 | EC | 1,2-B(ECO)E | | E-n-BC | EGB(TFE)E | | TEP | |
| 27 | EC | 1,2-B(ECO)E | | E-n-BC | | | | TEP |
| 28 | EC | 1,2-B(ECO)E | | E-n-BC | | | | EGB(TFE)E |

Electrolyte incombustibility, viscosity, high-temperature storage properties, non-aqueous secondary battery discharge capacity and internal resistance were evaluated using the electrolyte of Examples 16 to 28 in the same manner as Examples 1 to 15. However, discharge capacity was measured by charging under conditions of 4 hours at constant voltage and current of 4.2 V and 1 mA/cm$^2$, and discharging under conditions of a constant current of 0.5 mA/cm$^2$ and final voltage of 3.0 V. Those results are shown in Table 5.

TABLE 5

| Ex. No. | Combustion rate (mm/s) | Viscosity (cP) 20° C. | Coloring in High-temp. Shelf test | Discharge Capacity (mAh) | | | Internal Resistance (Ω) | | Capacity Maintenance Rate (%) | |
|---|---|---|---|---|---|---|---|---|---|---|
| | | | | 20° C. | 60° C. | 0° C. | Init. value | After 50 cycles | 20° C. | 60° C. |
| 16 | <0.1 | 8.6 | No | 1.49 | 1.63 | 1.46 | 6.9 | 7.8 | 95.2 | 78.6 |
| 17 | <0.1 | 9.2 | No | 1.54 | 1.67 | 1.51 | 7.1 | 8 | 95.7 | 78.9 |
| 18 | <0.1 | 8.8 | No | 1.47 | 1.63 | 1.43 | 7.4 | 8 | 94.8 | 78.2 |
| 19 | <0.1 | 8.4 | No | 1.43 | 1.59 | 1.39 | 7.7 | 8.3 | 94.4 | 77.4 |
| 20 | <0.1 | 9.1 | No | 1.41 | 1.57 | 1.35 | 7.5 | 8.1 | 94.6 | 77.7 |
| 21 | <0.1 | 8.9 | No | 1.36 | 1.56 | 1.32 | 8.2 | 9 | 93.1 | 76.8 |
| 22 | 6.9 | 7.8 | Yes | 1.57 | 1.7 | 1.52 | 6.8 | 7.5 | 96.4 | 79.1 |
| 23 | <0.1 | 10.2 | Yes | 1.06 | 1.23 | 0.81 | 10.6 | 20.9 | 68.7 | 45.9 |
| 24 | <0.1 | 6.3 | No | 0.59 | 0.78 | 0.53 | 8.2 | 10.7 | 60.3 | 40 |
| 25 | 0.7 | 8 | Yes | 1.48 | 1.52 | 1.44 | 8.5 | 9.2 | 92.9 | 64.6 |
| 26 | <0.1 | 11.1 | No | 1.21 | 1.34 | 1.16 | 11.3 | 15.1 | 87.6 | 70.3 |
| 27 | <0.1 | 8.3 | No | 1.5 | 1.62 | 1.47 | 9.1 | 13.8 | 95.3 | 78.1 |
| 28 | 3.2 | 8.5 | No | 1.53 | 1.64 | 1.51 | 7.2 | 8.2 | 96.2 | 78.5 |

As shown in Table 5, in Examples 16 to 21, combustion rates were less than 0.1 mm/s, indicating high electrolyte stability (incombustibility). Moreover, there were no color changes in the electrolyte in the high-temperature shelf test, and high values were demonstrated for both discharge capacity and discharge maintenance rate. In addition, electrolyte viscosity remained within a nearly constant range, there was little change in discharge capacity due to temperature changes, increases in battery internal resistance following 50 cycles of repeated charging and discharging were small, and the electrolyte exhibited excellent charge maintenance rates. Thus, these electrolyte can be expected to improve the output characteristics of batteries in which they are used. On the basis of the above, secondary batteries using the non-aqueous electrolyte of these examples are able to satisfy requirements for both battery performance and safety performance in good balance.

In contrast, in the electrolyte of a mixed solvent of equal volumes of ethylene carbonate and diethyl carbonate of Examples 22, although this electrolyte demonstrates high battery performance, the combustion rate is high at 6.9 mm/s, thus presenting a problem with safety. Conversely, in the mixed solvent of equal volumes of ethylene carbonate and triethyl phosphate of Example 23, although this electrolyte satisfies safety performance requirements, due to the large value of internal resistance as shown in Table 4, it has the problem of decreasing battery performance.

In Example 24, since the electrolyte does not contain a cyclic carbonate compound having a high dielectric constant, the electrical conductivity of the electrolyte decreases, thus resulting in a significant decrease in battery discharge capacity even among the comparative examples (Examples 22 to 28). In addition, in Example 25, which does not contain an alkylene bis-carbonate compound having excellent storage properties at high temperatures, the electrolyte is subjected to a side reaction causing it to become colored in the high-temperature shelf test. Moreover, in Example 26, which only contains 10 vol % of alkyl monocarbonate compound that is responsible for lowering viscosity, battery internal resistance increases due to the increase in viscosity of the electrolyte, thereby resulting in a decrease in battery capacity. In addition, in Example 27, which does not contain glycol diether responsible for reducing battery internal resistance, although there are no problems with battery capacity and so forth, the increase in battery internal resistance lowers the output characteristics to a level below that of Examples 16 to 21. Finally, in Example 28, which does not contain a phosphorous-containing organic compound that improves the safety of the electrolyte, the combustion rate is 3.2 mm/s, which is not sufficient for ensuring electrolyte safety.

Based on the above results, it is clear that it is important to use a non-aqueous electrolyte solvent containing a mixture of five types of compounds consisting of a cyclic carbonate compound, alkylene bis-carbonate compound, alkyl mono-carbonate compound, glycol diether compound and phosphorous-containing organic compound as shown in Examples 16 to 21 in order to remarkably satisfy both battery performance and safety performance requirements.

The mixing ratios for the organic solvent of the electrolyte are such that the ethylene carbonate compound is preferably mixed at 20 to 50 vol %, and more preferably 30 vol %, in consideration of the dielectric constant of the electrolyte. Since high-temperature storage properties decrease if the alkylene bis-carbonate compound is not added, it is preferably mixed at 5 to 35 vol %, and m ore preferably at 10 to 20 vol %.

In addition, although mixing in as much alkyl monocarbonate compound as possible results in greater improvement of performance since it is responsible for lowering viscosity, it is preferably mixed at 30 to 50 vol % in consideration of safety. Glycol diether compound, which is able to lower battery internal resistance, is preferably mixed at 5 to 35 vol %. Finally, although it is desirable to mix in as much of the phosphorous-containing organic compound as possible to improve safety, it is preferably mixed at 5 to 35 vol % due to the risk of lowering performance.

The use of a non-aqueous electrolyte containing a mixture of the five types of organic solvents or organic compounds in the mixing ratios described above makes it possible to obtain the proper balance between battery performance and safety in the resulting non-aqueous electrolytic secondary battery, enabling such a battery to be used in a wide range of applications.

EXAMPLES 29 TO 34

$LiPF_6$ was dissolved in a mixed solvent of equal volumes of ethylene carbonate (EC) ethylmethyl carbonate (EMC) and glycol diether (Nos. 1 to 6) to a concentration of 1 mole/liter to prepare electrolyte.

EXAMPLE 35

$LiPF_6$ was dissolved in a mixed solvent containing EC, EMC and glycol diether (No. 5) at a ratio of 40:50:10 (volume ratios) to a concentration of 1 mole/liter to prepare an electrolyte.

EXAMPLE 36

$LiPF_6$ was dissolved in a mixed solvent containing EC, EMC and glycol diether (No. 5) at a ratio of 40:20:40 (volume ratios) to a concentration of 1 mole/liter to prepare an electrolyte.

EXAMPLE 37

$LiPF_6$ was dissolved in a mixed solvent of equal volumes of EC and EMC to a concentration of 1 mole/liter to prepare an electrolyte.

EXAMPLE 38

$LiPF_6$ was dissolved in a mixed solvent of equal volumes of EC, EMC and dimethoxy ethane (DME) to a concentration of 1 mole/liter to prepare an electrolyte.

EXAMPLES 39 TO 44

$LiPF_6$ was dissolved in a mixed solvent of equal volumes of EC, triethyl phosphate (TEP) and glycol diether (Nos. 1 to 6) to a concentration of 1 mole/liter to prepare electrolyte.

EXAMPLE 45

$LiPF_6$ was dissolved in a mixed solvent containing EC, EMC, TEP and glycoldiether (No. 5) at a ratio of 40:40:10:10 (volume ratios) to a concentration of 1 mole/liter to prepare an electrolyte.

EXAMPLE 46

$LiPF_6$ was dissolved in a mixed solvent of equal volumes of EC and TEP to a concentration of 1 mole/liter to prepare an electrolyte.

EXAMPLE 47

$LiPF_6$ was dissolved in a mixed solvent of equal volumes of EC, TEP and DME to a concentration of 1 mole/liter to prepare an electrolyte.

Discharge Capacity Measurement Method

After measuring battery internal resistance using the secondary battery shown in FIG. 1 having each of the non-aqueous electrolyte of the above-mentioned Examples 29 to 47 for the battery electrolyte, the battery was charged for 4 hours at a constant current and constant voltage of 1 mA/cm² and 4.2 V, and then discharged at a constant current of 0.5 mA/cm² and final voltage of 3.0 V. Discharge capacity was then measured through 50 cycles of this charging and discharging. Battery internal resistance was also measured following measurement of discharge capacity.

The discharge capacity, internal resistance and capacity maintenance rate after 50 cycles of charging and discharging of the batteries of Examples 29 to 47 are shown in Table 6.

TABLE 6

| Example No. | Electrolytic Salt | Battery Internal Resistance (Ω) Initial value | Battery Internal Resistance (Ω) After 50 cycles | Capacity Maint. Rate (%) |
|---|---|---|---|---|
| 29 | EC + EMC + No. 1 (1:1:1) | 5.9 | 7.1 | 96.5 |
| 30 | EC + EMC + No. 2 (1:1:1) | 6.2 | 7.3 | 95.8 |
| 31 | EC + EMC + No. 3 (1:1:1) | 6.2 | 7.2 | 95.9 |
| 32 | EC + EMC + No. 4 (1:1:1) | 5.7 | 6.6 | 96.3 |
| 33 | EC + EMC + No. 5 (1:1:1) | 5.8 | 6.9 | 96.8 |
| 34 | EC + EMC + No. 6 (1:1:1) | 6.0 | 7.1 | 96.2 |
| 35 | EC + EMC + No. 5 (4:5:1) | 6.1 | 7.2 | 96.3 |
| 36 | EC + EMC + No. 5 (4:4:2) | 5.9 | 7.0 | 96.5 |
| 37 | EC + EMC (1:1) | 7.2 | 8.3 | 95.3 |
| 38 | EC + EMC + DME (1:1:1) | 6.8 | 8.0 | 95.5 |
| 39 | EC + TEP + No. 1 (1:1:1) | 8.3 | 9.6 | 93.5 |
| 40 | EC + TEP + No. 2 (1:1:1) | 8.6 | 10.4 | 91.3 |
| 41 | EC + TEP + No. 3 (1:1:1) | 8.6 | 10.2 | 91.4 |
| 42 | EC + TEP + No. 4 (1:1:1) | 8.2 | 9.4 | 91.6 |
| 43 | EC + TEP + No. 5 (1:1:1) | 8.4 | 9.6 | 93.9 |
| 44 | EC + TEP + No. 6 (1:1:1) | 8.5 | 9.8 | 92.6 |
| 45 | EC + EMC + TEP + No. 5 (4:4:1:1) | 6.5 | 7.8 | 94.7 |
| 46 | EC + TEP (1:1) | 10.6 | 20.9 | 68.7 |
| 47 | EC + TEP + DME (1:1:1) | 9.6 | 16.3 | 82.4 |

In comparison with Example 37, to which glycol diether was not added, in Examples 29 to 36 (present invention), to which glycol diether substituted with halogen of the present invention was added, both initial battery internal resistance and that after 50 cycles of charging and discharging were maintained at a low level, thus clearly indicating that output characteristics are maintained at a high level not only initially but also after 50 cycles of charging and discharging. In addition, the capacity maintenance rates after 50 cycles of charging and discharging of Examples 29 to 36 were also better than Example 37, thus confirming that the halogen-substituted glycol diethers of the present invention are effective in improving cycle characteristics. On the other hand, in Example 38, to which glycol diether not containing a halogen atom was added, the results were not significantly different from Example 37, thus clearly showing that the effect of an electrolyte containing halogen-substituted glycol diether of the present invention is extremely specific.

In addition in the case of adding halogen-substituted glycol diether of the present invention in Examples 39 to 45 and Examples 46 and 47 in which phosphate ester was used to improve safety, in comparison with Example 46, which does not contain glycol diether, and Example 47, which contains glycol diether not having a halogen atom, in Examples 39 to 45, battery internal resistance was held to a remarkably low level both initially and after 50 cycles of charging and discharging, while capacity maintenance rates after 50 cycles of charging and discharging were clearly maintained at a high level.

What is claimed is:

1. A battery non-aqueous electrolyte comprising an organic solvent comprising an electrolytic salt dissolved therein, wherein said organic solvent contains at least one type each of cyclic carbonate compounds, alkylene bis-carbonate compounds represented by chemical formula (2), alkyl mono-carbonate compounds represented by chemical formula (1), glycol diether compounds represented by chemical formula (3) and phosphorous-containing organic compounds:

$$R^3OC(=O)OR^4OC(=O)OR^5 \qquad (2)$$

wherein, substitution groups $R^3$ and $R^5$ represent identical or different alkyl groups and have 1 to 4 carbon atoms, and $R^4$ represents a straight chain or branched alylene group having 1 to 3 carbon atoms;

$$R^1OC(=O)OR^2 \qquad (1)$$

wherein, substitution groups $R^1$ and $R^2$ represent identical or different alkyl groups, and at least one of these has at least three carbon atoms; and:

$$R^6O-(R^7O)_n-R^8 \qquad (3)$$

wherein, substitution groups $R^6$ and $R^8$ are alkyl groups having 1 to 8 carbon atoms that may or may not be substituted with a halogen atom, substitution group $R^7$ is an alkylene group having 2 to 4 carbon atoms that may or may not be substituted with a halogen atom, and n is $1 \leq n \leq 4$, provided that at least one of substitution groups $R^6$, $R^7$ and $R^8$ is substituted with a halogen atom.

2. A non-aqueous electrolyte according to claim 1 wherein said alkylene bis-carbonate compound, said glycol diether compound and said phosphorous-containing organic compound are each contained at 5 to 35 vol % assuming the total amount of said organic solvent to be 100 vol %.

3. A non-aqueous electrolyte according to claim 1 wherein said cyclic carbonate compound is contained at 20 to 50 vol % assuming the total amount of said organic solvent to be 100 vol %.

4. A non-aqueous electrolyte according to claim 1 wherein said alkyl mono-carbonate compound is contained at 30 to 50 vol % assuming the total amount of said organic solvent to be 100 vol %.

5. A non-aqueous electrolyte according to claim 1 wherein said phosphorous-containing organic compound contains at least one type of organic compound selected from the group consisting of phosphate ester, phosphonate ester and phosphinate ester.

6. A non-aqueous electrolyte according to claim 1 wherein said electrolytic salt is comprised of one type or a combination of two or more types selected from the group consisting of inorganic salts composed of lithium ion and anion selected from the group consisting of $PF_6^-$, $BF_4^-$, $ClO_4^-$ and $AsF_6^-$, and organic salts composed of lithium ion and anion selected from the group consisting of $SO_3CF_3^-$, $N(CF_3SO_2)_2^-$, $C(CF_3SO_2)_3^-$ and their derivatives.

7. A non-aqueous electrolytic battery having a non-aqueous electrolyte, positive electrode and negative electrode, wherein an organic solvent of said non-aqueous electrolyte contains at least one type each of cyclic carbonate compounds, alkylene bis-carbonate compounds represented by chemical formula (2), alkyl mono-carbonate compounds represented by chemical formula (1), glycol diether compound represented by chemical formula (3) and phosphorous-containing organic compounds:

$$R^3OC(=O)OR^4OC(=O)OR^5 \quad (2)$$

wherein, substitution groups $R^3$ and $R^5$ represent identical or different alkyl groups and have 1 to 4 carbon atoms, and $R^4$ represents a straight chain or branched alkylene group having 1 to 3 carbon atoms;

$$R^1OC(=O)OR^2 \quad (1)$$

wherein, substitution groups $R^1$ and $R^2$ represent identical or different alkyl groups, and at least one of these has at least three carbon atoms; and:

$$R^6O-(R^7O)_n-R^6 \quad (3)$$

wherein, substitution groups $R^6$ and $R^8$ are alkyl groups having 1 to 8 carbon atoms that may or may not be substituted with a halogen atom, substitution group $R^7$ is an alkylene group having 2 to 4 carbon atoms that may or may not be substituted with a halogen atom, and n is $1 \leq n \leq 4$, provided that at least one of substitution groups $R^6$, $R^7$ and $R^8$ is substituted with a halogen atom.

* * * * *

UNITED STATES PATENT AND TRADEMARK OFFICE
CERTIFICATE OF CORRECTION

| | |
|---|---|
| PATENT NO. | : 6,566,015 B1 |
| DATED | : May 20, 2003 |
| INVENTOR(S) | : Manabu Yamada et al. |

It is certified that error appears in the above-identified patent and that said Letters Patent is hereby corrected as shown below:

<u>Title page,</u>
Item [57], ABSTRACT, should be as follows:

--The present invention provides a non-aqueous electrolyte comprising dissolving of a supporting electrolyte in an organic solvent, wherein said organic solvent contains cyclic carbonate compound, at least one type of alkyl mono-carbonate compound represented by chemical formula (1) ($R^1OC(=O)OR^2$) and alkylene bis-carbonate compound represented by chemical formula (2) ($R^3OC(=O)OR^4OC(=O)R^5$), and phosphorous-containing organic compound. The present invention also discloses a secondary battery that uses the above electrolyte wherein, since each compound does not inhibit the function of the others, enabling each compound to demonstrate its own function efficiently, battery performance is excellent, battery performance is maintained at a high level even at temperatures outside room temperature, and extremely excellent incombustibility is obtained.

The present invention also provides a non-aqueous electrolyte for batteries comprising the dissolving of an electrolytic salt in an organic solvent, wherein said organic solvent contains at least one type each of cyclic carbonate compound, alkyl mono-carbonate compound represented by chemical formula (1), alkylene bis-carbonate compound represented by chemical formula (2), glycol diether compound represented by chemical formula (3) ($R^6O-(R^7O)_n-R^8$) and phosphorous-containing organic compound; and a non-aqueous electrolytic secondary battery that uses the above non-aqueous electrolyte. The non-aqueous electrolyte maintains the battery characteristics of a secondary battery and satisfies both high battery performance and safety in good balance.

The present invention also provides a non-aqueous electrolyte for a battery comprising dissolving of an electrolytic salt in an organic solvent, wherein said organic solvent contains at least one type of compound selected from the group of glycol diethers represented by the general formula (4) $R^9O-(R^{10}O)_n-R^{11}$. The use of at least one type of glycol diether represented with this general formula is able to yield satisfactory output characteristics by lowering the internal resistance of the battery as a result of increasing the mobility of lithium ions at the solid-liquid interface.--

UNITED STATES PATENT AND TRADEMARK OFFICE
CERTIFICATE OF CORRECTION

PATENT NO.   : 6,566,015 B1
DATED        : May 20, 2003
INVENTOR(S)  : Manabu Yamada et al.

It is certified that error appears in the above-identified patent and that said Letters Patent is hereby corrected as shown below:

Column 30,
Line 1, (FORMULA 3), second occurrence of "$R^6$" should be -- $R^8$ --.

Signed and Sealed this

Twentieth Day of July, 2004

JON W. DUDAS
*Acting Director of the United States Patent and Trademark Office*